United States Patent [19]

Ito et al.

[11] Patent Number: 5,126,337
[45] Date of Patent: Jun. 30, 1992

[54] THIAZETOQUINOLINE-3-CARBOXYLIC ACID DERIVATIVE AND A PHARMACEUTICAL COMPOSITION COMPRISING THE SAME

[75] Inventors: Yasuo Ito, Katsuyama; Hideo Kato, Fukui; Eiichi Koshinaka, Katsuyama; Nobuo Ogawa, Katsuyama; Noriyuki Yagi, Katsuyama; Toshihiko Yoshida; Tomio Suzuki, both of Fukui, all of Japan

[73] Assignee: Hokuriku Pharmaceutical Co., Ltd., Katsuyama, Japan

[21] Appl. No.: 505,138

[22] Filed: Apr. 5, 1990

[30] Foreign Application Priority Data

| | | |
|---|---|---|
| Apr. 18, 1989 [JP] | Japan | 1-96328 |
| Aug. 31, 1989 [JP] | Japan | 1-223217 |
| Oct. 16, 1989 [JP] | Japan | 1-264840 |

[51] Int. Cl.⁵ .............. A61K 31/47; C07D 513/14
[52] U.S. Cl. ......................... 514/210; 546/80
[58] Field of Search ...................... 546/80; 514/210

[56] References Cited

U.S. PATENT DOCUMENTS

| 4,843,070 | 6/1989 | Kise et al. | 546/80 |
| 5,011,831 | 4/1991 | Kise et al. | 514/210 |

FOREIGN PATENT DOCUMENTS

| 0315827 | 5/1989 | European Pat. Off. | 546/80 |
| 0107990 | 5/1988 | Japan | 546/80 |

OTHER PUBLICATIONS

J. March Advanced Organic Chemistry John Wiley and Sons, Inc., New York, 1985, pp. 476-479, 590-591.

*Primary Examiner*—Mary C. Lee
*Assistant Examiner*—Michael G. Ambrose
*Attorney, Agent, or Firm*—Oblon, Spivak, McClelland, Maier & Neustadt

[57] ABSTRACT

A thiazetoquinoline-3-carboxylic acid derivative represented by the general formula (I)

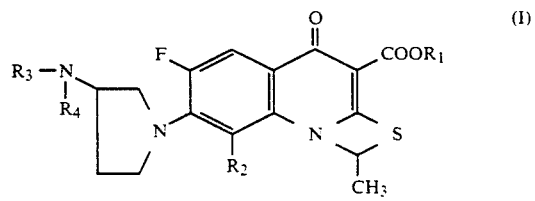

wherein $R_1$ is a hydrogen atom or a lower alkyl group; $R_2$ is a fluorine atom or a chlorine atom; $R_3$ is a hydrogen atom, a lower alkyl group, a lower alkanoyl group, a halogenated lower alkanoyl, or alkoxycarbonyl group; and $R_4$ is a hydrogen atom or a lower alkyl group, and a pharmacologically acceptable salt thereof, a process for preparation thereof, a pharmaceutical composition comprising the same, and a method for the treatment of an infectious disease by administering the same, are disclosed.

11 Claims, No Drawings

THIAZETOQUINOLINE-3-CARBOXYLIC ACID DERIVATIVE AND A PHARMACEUTICAL COMPOSITION COMPRISING THE SAME

BACKGROUND OF THE INVENTION

1. Field of the Invention

The present invention relates to a novel thiazetoquinoline-3-carboxylic acid derivative and a pharmacologically acceptable salt thereof which has an excellent antibacterial activity and is useful as a synthetic antibacterial agent, and to the method for preparation thereof.

The present invention also relates to a pharmaceutical composition comprising the effective amount of the same which is useful for the treatment of an infectious disease.

More particularly, the present invention relates to a thiazetoquinoline-3-carboxylic acid derivative represented by the following general formula (I):

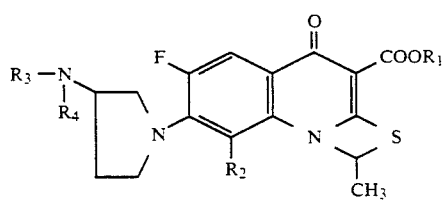

wherein $R_1$ is a hydrogen atom or a lower alkyl group; $R_2$ is a fluorine atom or a chlorine atom; $R_3$ is a hydrogen atom, a lower alkyl group, a lower alkanoyl group, a halogenated lower alkanoyl, or alkoxycarbonyl group; and $R_4$ is a hydrogen atom or a lower alkyl group. The present invention also relates to a pharmacologically acceptable salt of compounds of general formula (I), a process for preparing the same, and a pharmaceutical composition comprising the same together with a pharmaceutically acceptable carrier or coating.

2. Description of the Prior Art

Since the development of nalidixic acid, pyridonecarboxylic acids antibacterials have become the chief, most widely used antibacterial chemotherapeutants for the clinical treatment of an infectious diseases such as urinary tract infection, intestinal infection and cholangia infection.

Recently, norfloxacin (The Merck Index, 11th Edition, 6617), ofloxacin (The Merck Index, 11th Edition, 6688), and ciprofloxacin (The Merck Index, 11th Edition, 2315) represented by the following formula (II):

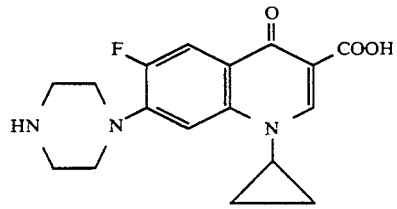

were synthesized successively and have been found to have excellent antibacterial activities and a wide antibacterial spectra compared with known synthetic antibacterials. These compounds have been developed as antibacterial agents on the market for the clinical treatment of prostatitis, or otolaryngologic, internal, ophthalmologic, and dental infections as well as the above-mentioned infectious diseases.

Japanese Unexamined Patent Publication No. 107990/1988 discloses 6-fluoro-1-methyl-4-oxo-7-(1-piperazinyl)-1H,4H-[1,3]thiazeto[3,2-a]quinoline-3-carboxylic acid represented by the following formula (III):

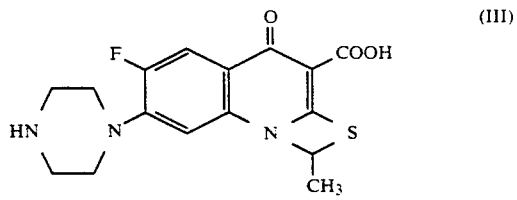

Japanese Unexamined Patent Publication No. 230584/1989 discloses 6,8-difluoro-1-methyl-4-oxo-7-(1-piperazinyl)-1H,4H-[1,3]thiazeto[3,2-a]quinoline-3-carboxylic acid represented by the following formula (IV):

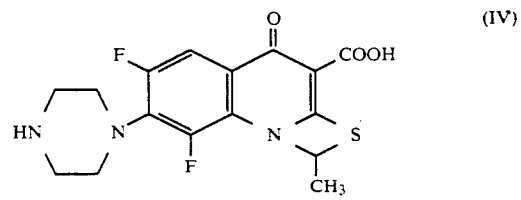

Japanese Unexamined Patent Publication No. 107990/1988 discloses 7-(3-amino-1-pyrrolidinyl)-6-fluoro-1-methyl-4-oxo-1H,4H-[1,3]thiazeto[3,2-a]quinoline-3-carboxylic acid represented by the following formula (V):

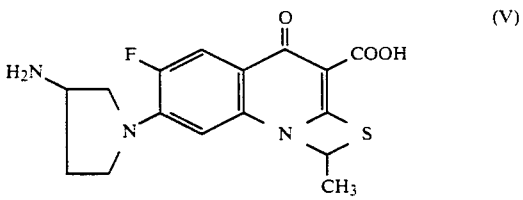

Japanese Unexamined Patent Publication No. 230584/1989 discloses 7-(3-amino-1-pyrrolidinyl)-6,8-difluoro-4-oxo-1H,4H-[1,3]thiazeto[3,2-a]quinoline-3-carboxylic acid represented by the following formula (VI):

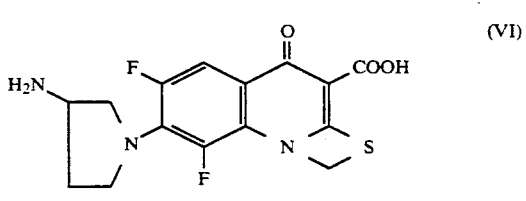

However, none of the above documents discloses a thiazetoquinoline compound having substituents of a methyl group, an aminopyrrolidinyl group, and a halogen atom in the 1, 7, and 8 positions of the thiazetoquinoline ring, respectively. Further, the utility of an optically active aminopyrrolidinyl substituent is not taught by any prior art.

Pyridonecarboxylic acid antibacterials have been remarkably improved since the discovery of norfloxacin, and have been found to be useful for the clinical treatment of various kinds of infections diseases including urinary tract infection. The mode of antibacterial action of the pyridonecarboxylic acid antibacterials is believed to be an inhibitory action against DNA gyrase which is classified as a DNA topoisomerase. It is also believed that a bacterial resistance against a pyridonecarboxylic acid is not transmitted to other bacteria via plasmid DNAs, unlike other antibiotics.

Clinically, however, low-sensitive strains against the pyridonecarboxylic acids have found to be increasing, and the developed antibacterials has become ineffective for the treatment of intractable diseases such as for example a chronic infection caused by Pseudomonas aeruginosa or Gram-positive bacterial infections. Furthermore, some pyridonecarboxylic acid antibacterial agents have been revealed to cause convulsions when used in combination with certain anti-inflammatory agents.

Therefore, the above-mentioned, presently available antibacterials are insufficient from a clinical point of view. Much improvement has been longed for with respect to (1) antibacterial activities against clinically isolated resistant bacteria and (2) safety of administration, e.g., eliminating possible convulsions caused by administration with an anti-inflammatory agent.

SUMMARY OF THE INVENTION

An object of the present invention is to provide a novel pyridonecarboxylic acid derivative having excellent antibacterial activities against clinically isolated bacteria as well as against standard laboratory strains.

Another object of the present invention is to provide a low-toxicity pyridonecarboxylic acid derivative which eliminates adverse reactions such as convulsions when administered in combination with an anti-inflammatory agent.

A further object of the present invention is to provide a pharmaceutical composition comprising said pyridonecarboxylic acid derivative which is useful for the treatment of various kinds of bacterial infections.

The inventors of the present invention have conducted various studies to achieve the foregoing objects and found that the objects can effectively attained by providing a novel thiazetoquinoline-3-carboxylic acid derivative which is substituted with a methyl group, an aminopyrrolidinyl group, and a halogen atom in the 1, 7, and 8 positions of the thiazetoquinoline ring, respectively. The novel derivative has potent antibacterial activity against various kinds of bacteria including clinically isolated resistant bacteria, and does not induce convulsion as used in combination with an anti-inflammatory agent.

The present invention provides a novel thiazetoquinoline-3-carboxylic acid derivative represented by the general formula (I),

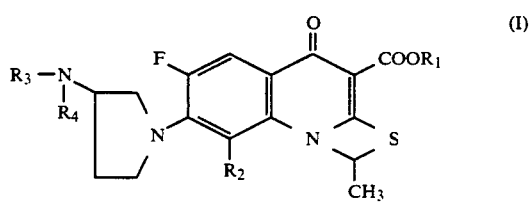

(I)

wherein $R_1$ is a hydrogen atom or a lower alkyl group; $R_2$ is a fluorine atom or a chlorine atom; $R_3$ is a hydrogen atom, a lower alkyl group, a lower alkanoyl group, or a halogenated lower alkanoyl, or alkoxycarbonyl group; and $R_4$ is a hydrogen atom or a lower alkyl group, and pharmacologically acceptable salts of the above compounds. The present invention also provides a process for preparing the compounds of general formula (I), and a pharmaceutical composition comprising an effective amount of the same.

DETAILED DESCRIPTION OF THE INVENTION

In the general formula (I), examples of the lower alkyl group represented by $R_1$, $R_3$, and $R_4$ (I) include methyl, ethyl, n-propyl, isopropyl, n-butyl, sec-butyl, and tert-butyl groups; examples of the lower alkanoyl group represented by $R_3$ include formyl, acetyl, propanoyl, butyroyl, and trimethylacetyl groups; examples of the halogenated alkanoyl group represented by $R_3$ include fluoroacetyl, difluoroacetyl, trifluoroacetyl, chloroacetyl, dichloroacetyl, and trichloroacetyl groups; and examples of the alkoxycarbonyl group represented by $R_3$ include benzyloxycarbonyl, ethoxycarbonyl, methoxycarbonyl, and tert-butoxycarbonyl groups.

Particularly preferred examples of the present invention include:
7-((S)-3-amino-1-pyrrolidinyl)-6,8-difluoro-1-methyl-4-oxo-1H,4H-[1,3]thiazeto[3,2-a]quinoline-3-carboxylic acid;
7-((S)-3-amino-1-pyrrolidinyl)-8-chloro-6-fluoro-1-methyl-4-oxo-1H,4H-[1,3]thiazeto[3,2-a]quinoline-3-carboxylic acid;
7-(3-amino-1-pyrrolidinyl)-6,8-difluoro-1-methyl-4-oxo-1H,4H-[1,3]thiazeto[3,2-a]quinoline-3-carboxylic acid;
7-(3-amino-1-pyrrolidinyl)-8-chloro-6-fluoro-1-methyl-4-oxo-1H,4H-[1,3]thiazeto[3,2-a]quinoline-3-carboxylic acid;
7-((R)-3-amino-1-pyrrolidinyl)-8-chloro-6-fluoro-1-methyl-4-oxo-1H,4H-[1,3]thiazeto[3,2-a]quinoline-3-carboxylic acid;
7-((R)-3-amino-1-pyrrolidinyl)-6,8-difluoro-1-methyl-4-oxo-1H,4H-[1,3]thiazeto[3,2-a]quinoline-3-carboxylic acid;
Ethyl 7-((S)-3-amino-1-pyrrolidinyl)-8-chloro-6-fluoro-1-methyl-4-oxo-1H,4H-[1,3]thiazeto[3,2-a]quinoline-3-carboxylate;
Ethyl 7-((S)-3-amino-1-pyrrolidinyl)-6,8-difluoro-1-methyl-4-oxo-1H,4H-[1,3]thiazeto[3,2-a]quinoline-3-carboxylate;
7-((S)-3-dimethylamino-1-pyrrolidinyl)-6,8-difluoro-1-methyl-4-oxo-1H,4H-[1,3]thiazeto[3,2-a]quinoline-3-carboxylic acid;
8-chloro-7-((S)-3-dimethylamino-1-pyrrolidinyl)-6-fluoro-1-methyl-4-oxo-1H,4H-[1,3]thiazeto[3,2-a]quinoline-3-carboxylic acid;
8-chloro-6-fluoro-1-methyl-7-((S)-3-methylamino-1-pyrrolidinyl)-4-oxo-1H,4H-[1,3]thiazeto[3,2-a]quinoline-3-carboxylic acid;
6,8-difluoro-1-methyl-7-((S)-3-methylamino-1-pyrrolidinyl)-4-oxo-1H,4H-[1,3]thiazeto[3,2-a]quinoline-3-carboxylic acid;
6,8-difluoro-1-methyl-4-oxo-7-((S)-3-trifluoroacetylamino-1-pyrrolidinyl)-1H,4H-[1,3]thiazeto[3,2-a]quinoline-3-carboxylic acid;

8-chloro-6-fluoro-1-methyl-4-oxo-7-((S)-3-tri-fluoroacetylamino-1-pyrrolidinyl)-1H,4H-[1.3]thiazeto[3,2-a]quinoline-3-carboxylic acid;

7-[(S)-3-(tert-butoxycarbonylamino)-1-pyrrolidinyl]-6,8-difluoro-1-methyl-4-oxo-1H,4H-[1,3]thiazeto[3,2-a]quinoline-3-carboxylic acid;

7-[(S)-3-(tert-butoxycarbonylamino)-1-pyrrolidinyl]-8-chloro-6-fluoro-1-methyl-4-oxo-1H,4H-[1.3]thiazeto[3,2-a]quinoline-3-carboxylic acid; and 7-(3-acetylamino-1-pyrrolidinyl)-6,8-difluoro-1-methyl-4-oxo-1H,4H-[1,3]thiazeto[3,2-a]quinoline-3-carboxylic acid.

The pharmacologically acceptable salts of the compound of the present invention represented by the general formula (I) may be acid addition salts or alkali addition salts. Examples of the acid addition salts include mineral acid salts such as for example hydrochloride, hydrobromide, hydroiodide, nitrate, sulfate, or phosphate, and organic acid salts such as for example acetate, maleate, fumarate, citrate, oxalate, malate, methanesulfonate, p-toluenesulfonate, mandelate, 10-camphorsulfonate, or tartarate. Examples of the alkali addition salts include inorganic alkali salts such as for example sodium, potassium, calcium, silver, zinc, lead, or ammonium salts, and organic alkali salts such as for example ethanolamine salt or N,N-dialkylethanolamine salt.

The thiazetoquinoline compound represented by the general formula (I) has more than one asymmetric carbon atom in the molecule, and any optically active compounds and diastereoisomers as well as racemates and the mixtures of the diastereoisomers are incorporated within the scope of the present invention.

According to the present invention, various methods for preparing the novel thiazetoquinoline compound represented by the general formula (I) are provided.

According to one embodiment of the process of the present invention, the compounds represented by the above general formula (I) can be prepared by reacting in a solvent a 7-halogeno-thiazetoquinoline-3-carboxylic acid derivative of general formula (VII)

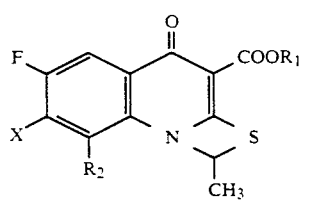

(VII)

wherein $R_1$ and $R_2$ are the same as those defined above and X represents a halogen atom, with a 3-aminopyrrolidine compound represented by the general formula (VIII)

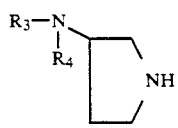

(VIII)

wherein $R_3$ and $R_4$ are the same as those defined above, in the presence of or absence of a base, and followed by hydrolysis, if necessary.

Any suitable inert solvent may be used in the process of the present invention. Examples of the inert solvent include alcohols such as for example methanol, ethanol, n-propanol, isopropanol, or n-butanol; aprotic polar solvents such as for example acetonitrile, N,N-dimethylformamide, N-methyl-2-pyrrolidone, dimethyl sulfoxide, or hexamethylphospholic triamide; aromatic hydrocarbons such as for example benzene and toluene; organic bases such as for example pyridine, picoline, lutidine, and collidine; and mixtures of the above solvents.

An organic base such as for example triethylamine or 1,8-diazabicyclo[5.4.0]-7-undecene, or an inorganic base such as for example sodium carbonate or potassium carbonate may be used as the base. The reaction may be carried out at a temperature of from an ice-cooled temperature to the reflux temperature of the reaction solvent used.

The hydrolysis may be carried out according to a known method in the presence of an acid or an alkali. An acid such as for example hydrochloric acid, sulfuric acid, or fuming sulfuric acid may be used in an acidic hydrolysis reaction; and a base such as for example sodium hydroxide or potassium hydroxide may be used in an alkaline hydrolysis reaction. These acids or bases may be used in the form of an aqueous solution, an alcoholic solution such as for example methanolic, ethanolic, n-butanolic, sec-butanolic, or tert-butanolic solution, or a solution of an aqueous organic solvent. The hydrolysis reaction may be carried out at a temperature of from room temperature to the reflux temperature of the reaction solvent used.

The 7-halogeno-thiazetoquinoline-3-carboxylic acid represented by the above general formula (VII) which is used in the present process can be prepared according to the following scheme, wherein $R_1$ and $R_2$ are the same as those defined above:

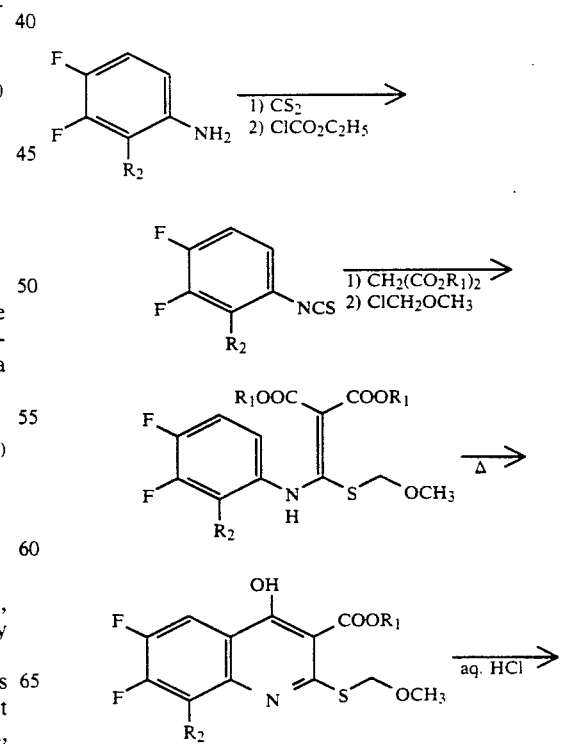

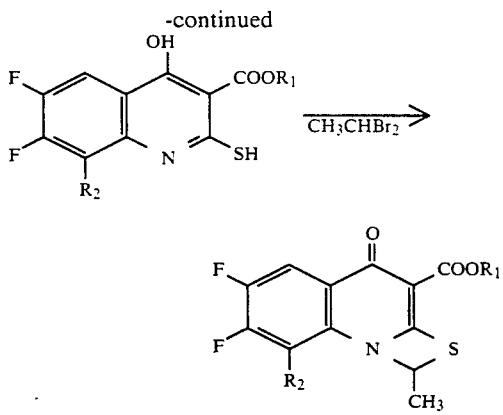

According to another aspect of the present invention, the compounds represented by the general formula (I) wherein $R_2$ is a chlorine atom can be prepared by treating the compound represented by the general formula (IX).

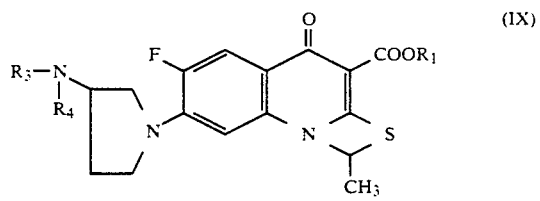

wherein $R_1$, $R_3$, and $R_4$ are the same as those defined above, with a chlorinating agent, and followed by hydrolysis, if necessary.

Examples of the chlorinating agent used in the above process include chlorine gas and sulfuryl chloride. A solvent such as for example chloroform, dichloromethane, 1,2-dichloroethane, chlorosulfonic acid, or acetic acid may be used. The chlorinating reaction may be carried out at a temperature of from an ice-cooled temperature to the reflux temperature of the solvent used.

The hydrolysis may be carried out according to a known method in the presence of an acid or an alkali. An acid such as for example hydrochloric acid, sulfuric acid, or fuming sulfuric acid may be used in an acidic hydrolysis reaction, and a base such as for example sodium hydroxide or potassium hydroxide may be used in an alkaline hydrolysis reaction. The acid or the base may be used in the form of an aqueous solution, an alcoholic solution such as for example methanolic, ethanolic, n-butanolic, sec-butanolic, or tert-butanolic solution, or a solution of an aqueous organic solvent. The hydrolysis reaction may be carried out at a temperature of from room temperature to the reflux temperature of the reaction solvent used.

The novel thiazetoquinoline-3-carboxylic acid derivatives represented by the general formula (I) or pharmacologically acceptable salts thereof produced according to the method described above have potent antibacterial activity against gram-positive and gram-negative bacteria. These compounds of the present invention are also useful for the treatment of various kinds of infectious diseases. The thiazetoquinoline-3-carboxylic acid derivative of the present invention may preferably be administered orally or parenterally to a patient as a pharmaceutical composition comprising the effective amount of the said thiazetoquinoline derivative together with a pharmaceutically acceptable carrier or coating.

The pharmaceutical composition of the present invention may be in the form of capsule, tablet, subtilized granule, granule, powder, or syrup for oral administration, or in the form of an injection, suppository, eye drop, eye ointment, otic solution, or dermatologic dosage form. The pharmaceutical composition of the present invention can be prepared by an ordinary method which includes the admixture of a pharmacologically and pharmaceutically acceptable carrier or coating with said thiazetoquinoline-3-carboxylic acid derivative. For the preparation of the pharmaceutical composition suitable for oral administration or suppository, the carrier or coating may comprise a diluent such as for example lactose, D-mannitol, starch, or crystalline cellulose; a disintegrant such as for example carboxymethylcellulose or calcium carboxymethylcellulose, a binder such as for example hydroxypropylcellulose, hydroxypropylmethylcellulose, or polyvinylpyrrolidone; a lubricant such as for example magnesium stearate or talc; a coating agent such as for example hydroxypropylmethylcellulose or sucrose; or a base such as for example polyethyleneglycol or hard fat. The pharmaceutical composition of the present invention suitable for injection, or use as an eye drop or otic solution may comprise carriers such as, for example, a solubilizing agent or solubilizer, e.g., distilled water for injection, saline, or propylene glycol which is useful for an aqueous composition or a composition for preparing aqueous solution before use; a pH adjusting agent such as for example inorganic and organic acids or bases; tonicity agent; or stabilizer may be used. For the preparation of the pharmaceutical composition suitable for eye ointment or dermatologic medicine, a carrier or coating such as for example a pharmaceutical ingredient, e.g., white petrolatum, macrogol, glycerin, or cloth which is useful for ointment, cream, or cataplasmata may be used.

Use of the pharmaceutical composition of the present invention comprises administering the composition described above internally or externally to a patient. The dose of the pharmaceutical composition for an adult patient may generally be about from 10 to 1,000 mg per day for oral administration or about from 1 to 500 mg per day for parenteral administration, which may be increased or decreased depending on the conditions of the patient to be treated.

The effects of the compounds of the present invention are summarized in Tables 1, 2, and 3 with respect to antibacterial spectrum against clinically isolated bacteria as well as laboratory standard strains, convulsion inducing activity, and acute toxicity, respectively, whereby ciprofloxacin hydrochloride represented by the formula (II), 6-fluoro-1-methyl-4-oxo-7-(1-piperazinyl)-1H,4H-[1,3]thiazeto[3,2-a]quinoline-3-carboxylic acid (Japanese Patent Unexamined Publication No. 107990/1988) represented by formula (III), 6,8-difluoro-1-methyl-4-oxo-7-(1-piperazinyl)-1H,4H-[1,3]thiazeto[3,2-a]quinoline-3-carboxylic acid (Japanese Patent Unexamined Publication No. 230584/1989) represented by formula (IV), 7-(3-amino-1-pyrrolidinyl)-6-fluoro-1-methyl-4-oxo-1H,4H-[1,3]thiazeto[3,2-a]quinoline-3-carboxylic acid (Japanese Patent Unexamined Publication No. 107990/1988) represented by formula (V), and 7-(3-amino-1-pyrrolidinyl)-6,8-difluoro-4-oxo-1H,4H-[1,3]thiazeto[3,2-a]quinoline-3-carboxylic acid (Japanese Patent Unexamined Publication No. 230584/1989) represented by formula (VI) were used as reference drugs A, B, C, D, and E, respectively.

A. ANTIBACTERIAL SPECTRUM

Minimum inhibitory concentrations (MIC) of test compounds were determined by the twofold agar dilution method (Chemotherapy, 29(1), 76(1981)). Overnight cultures in Mueller-Hinton broth were suspended by buffered saline gelatin. One loopful of the bacterial suspension ($10^6$ or $10^8$ colony-forming units/ml) was incubated onto the plates containing test compounds. The plates were incubated for 18 hrs at 37° C. The MIC was defined by the lowest concentration of the drug that inhibited visible growth of bacteria. The results are summarized in Table 1.

The compounds of the present invention show excellent antibacterial activities compared with Reference Drugs against clinically isolated strains as well as standard laboratory strains.

TABLE 1-A

| Strain | Gram | Ex. 27 | Ex. 29 | Ex. 33 | Ex. 34 | Ex. 35 | Ex. 36 | Ex. 37 | Ex. 39 | Ref. Drug A | Ref. Drug B | Ref. Drug C | Ref. Drug D | Ref. Drug E |
|---|---|---|---|---|---|---|---|---|---|---|---|---|---|---|
| Antibacterial Spectrum (Standard Laboratory Strains) | | | | | | | | | | | | | | |
| Staphylococuss aureus FDA 209PJC-1 | + | 0.025 | 0.05 | 0.025 | 0.05 | 0.10 | 0.20 | 0.20 | 0.20 | 0.20 | 0.10 | 0.10 | 0.05 | 0.10 |
| Escherichia coli NIHJ JC-2 | − | 0.025 | 0.025 | 0.025 | 0.025 | 0.10 | 0.10 | 0.10 | 0.10 | 0.025 | 0.025 | 0.05 | 0.05 | 0.10 |
| Klebsiella pneumoniae PCI-602 | − | ≦0.003 | 0.006 | 0.012 | 0.012 | 0.05 | 0.025 | 0.05 | 0.025 | 0.012 | 0.012 | 0.025 | 0.012 | 0.05 |
| Serratia marcescens IAM 1184 | − | 0.05 | 0.10 | 0.10 | 0.05 | 0.20 | 0.20 | 0.39 | 0.39 | 0.10 | 0.05 | 0.10 | 0.10 | 0.20 |
| Pseudomonas aeruginosa IFO 3445 | − | 0.10 | 0.10 | 0.10 | 0.10 | 0.78 | 0.78 | 0.78 | 1.56 | 0.20 | 0.20 | 0.20 | 0.10 | 0.20 |
| Enterobacter cloacae 963 | − | 0.05 | 0.025 | 0.05 | 0.025 | 0.10 | 0.20 | 0.20 | 0.39 | 0.05 | 0.05 | 0.05 | 0.05 | 0.10 |
| Antibacterial Spectrum (Clinically Isolated Strains) | | | | | | | | | | | | | | |
| Staphylococuss aureus HPC 527 | + | 0.05 | 0.05 | 0.05 | 0.05 | 0.10 | 0.20 | 0.20 | 0.20 | 0.39 | 0.39 | 0.20 | 0.10 | 0.20 |
| Staphylococuss aureus HPC 308 | + | 0.78 | 0.78 | 0.78 | 0.78 | 0.78 | 1.56 | 3.13 | 1.56 | 25 | 25 | 6.25 | 25 | 100 |
| Staphylococuss aureus HPC 292 | + | 6.25 | 6.25 | 6.25 | 6.25 | 12.5 | 6.25 | 6.25 | 12.5 | 50 | 50 | 25 | >100 | >100 |
| Enterococcus faecalis HPC 984 | + | 0.20 | 0.20 | 0.20 | 0.20 | 0.39 | 0.78 | 0.78 | 0.39 | 0.39 | 0.78 | 0.39 | 0.39 | 0.78 |
| Enterococcus faecalis HPC 948 | + | 0.78 | 0.78 | 0.78 | 0.78 | 1.56 | 3.13 | 3.13 | 1.56 | 3.13 | 6.25 | 3.13 | 3.13 | 50 |
| Enterococcus faecalis HPC 975 | + | 6.25 | 6.25 | 6.25 | 12.5 | 12.5 | 6.25 | 12.5 | 12.5 | 50 | 50 | 50 | >100 | >100 |
| Enterobacter cloacae HNR 1939 | − | 0.20 | 0.20 | 0.20 | 0.20 | 0.39 | 0.78 | 0.78 | 0.78 | 0.78 | 0.20 | 0.39 | 0.39 | 0.78 |
| Enterobacter cloacae HNR 1946 | − | 0.20 | 0.20 | 0.20 | 0.20 | 0.39 | 0.78 | 1.56 | 0.78 | 0.78 | 0.39 | 0.39 | 0.78 | 1.56 |
| Enterobacter cloacae HNR 1941 | − | 1.56 | 1.56 | 3.13 | 1.56 | 6.25 | 25 | 25 | 12.5 | 25 | 12.5 | 6.25 | >100 | >100 |
| Acinetobacter calcoaceticus HNR 916 | − | 0.10 | 0.10 | 0.20 | 0.10 | 0.10 | 0.10 | 0.20 | 0.10 | 0.39 | 0.78 | 0.20 | 0.39 | 0.39 |
| Acinetobacter calcoaceticus HNR 939 | − | 1.56 | 1.56 | 1.56 | 1.56 | 1.56 | 0.78 | 1.56 | 1.56 | 6.25 | 6.25 | 3.13 | 6.25 | >100 |
| Acinetobacter calcoaceticus HNR 904 | − | 25 | 6.25 | 25 | 12.5 | 3.13 | 12.5 | 25 | 6.25 | 100 | >100 | 25 | >100 | >100 |
| Klebsiella pneumoniae HNR 858 | − | 0.20 | 0.20 | 0.20 | 0.20 | 0.39 | 0.78 | 0.78 | 0.78 | 0.78 | 0.20 | 0.39 | 0.39 | 0.78 |
| Klebsiella pneumoniae HNR 869 | − | 0.78 | 0.39 | 0.78 | 0.78 | 1.56 | 6.25 | 3.13 | 3.13 | 3.13 | 0.78 | 0.78 | 3.13 | 50 |
| Klebsiella pneumoniae HNR 828 | − | 1.56 | 1.56 | 3.13 | 3.13 | 6.25 | 12.5 | 12.5 | 12.5 | 12.5 | 1.56 | 3.13 | 50 | 50 |
| Serratia marcescens | − | 0.05 | 0.05 | 0.05 | 0.05 | 0.10 | 0.20 | 0.20 | 0.20 | 0.10 | 0.05 | 0.10 | 0.10 | 0.10 |

TABLE 1-A-continued

| Strain | Gram | Ex. 27 | Ex. 29 | Ex. 33 | Ex. 34 | Ex. 35 | Ex. 36 | Ex. 37 | Ex. 39 | Ref. Drug A | Ref. Drug B | Ref. Drug C | Ref. Drug D | Ref. Drug E |
|---|---|---|---|---|---|---|---|---|---|---|---|---|---|---|
| HNR 1544 | | | | | | | | | | | | | | |
| Serratia marcescens HNR 1792 | — | 1.56 | 0.78 | 1.56 | 1.56 | 3.13 | 12.5 | 12.5 | 12.5 | 6.25 | 6.25 | 3.13 | 50 | >100 |
| Serratia marcescens HNR 1767 | — | 6.25 | 3.13 | 12.5 | 6.25 | 12.5 | 25 | 25 | 12.5 | 50 | 50 | 12.5 | >100 | >100 |
| Pseudomonas aeruginosa HNR 1489 | — | 0.10 | 0.20 | 0.20 | 0.20 | 0.78 | 0.78 | 0.78 | 1.56 | 0.20 | 0.10 | 0.20 | 0.10 | 0.39 |
| Pseudomonas aeruginosa HNR 1472 | — | 3.13 | 3.13 | 6.25 | 3.13 | 12.5 | 50 | 50 | 25 | 12.5 | 6.25 | 6.25 | 50 | >100 |
| Pseudomonas aeruginosa HNR 1537 | — | 6.25 | 3.13 | 12.5 | 3.13 | 25 | 100 | 100 | 50 | 12.5 | 6.25 | 12.5 | 1.56 | >100 |

(MIC μg/ml: $10^6$ cfu/ml)

B. CONVULSION INDUCING ACTIVITY

Male mice of ddY strain, 5 weeks old, were used. Fenbufen suspended in 0.5% carboxymethyl cellulose was administered orally at a dose of 100 mg/kg. After thirty minutes, test compounds suspended in 0.5% carboxymethyl cellulose were injected intraperitoneally (i.p.) at a dose of 100 mg/kg or 300 mg/kg. From the results summarized in Table 2, it is understood that the compounds of the present invention do not cause any convulsion when administered together with fenbufen.

TABLE 2

| | Convulsion Inducing Activity | |
|---|---|---|
| | Number of convulsion induced/Number of animals | |
| Compound | 100 mg/kg (i.p.) | 300 mg/kg (i.p.) |
| Example 27 | 0/6 | 0/6 |
| Example 29 | 0/6 | 0/6 |
| Example 33 | 0/6 | 0/6 |
| Example 34 | 0/6 | 0/6 |
| Reference Drug A | 4/6 | 6/6 |
| Reference Drug B | 1/6 | 6/6 |
| Reference Drug C | 6/6 | — |
| Reference Drug D | 0/6 | 0/6 |

C. ACUTE TOXICITY

Male mice of ddY strain, 4 weeks old, were used. Test compounds were solved in 0.1N—NaOH solution and neutralized with 0.1N—HCl solution. Each compound was administered intravenously (i.v.) at a dose of 270 mg/kg. From the results summarized in Table 3, it is understood that the compounds of the present invention are less toxic than Reference Drug A (ciprofloxacin hydrochloride).

TABLE 3

| | Acute toxicity |
|---|---|
| Compound | Number of death/Number of animals <270 mg/kg (i.v.)> |
| Example 27 | 4/10 |
| Example 29 | 3/10 |
| Reference Drug A | 7/10 |

The following References and Examples are given by way of illustration only and are not to be contrued as limiting.

REFERENCE 1

2-Chloro-3,4-difluorophenyl isothiocyanate

To a mixture of 170 g of 2-Chloro-3,4-difluoroaniline and 434 ml of triethylamine, 86.3 g of carbon disulfide was added dropwise at room temperature and the mixture was stirred for 2 weeks. The precipitate was collected by filtration to give 234 g of yellow crystals. To a suspension of 156 g of the crystals and 70 g of triethylamine in 400 ml of dichloromethane, 48 ml of ethyl chlorocarbonate was added dropwise at from −5° C. to 5° C. After stirring for 30 minutes, ice water and 60 ml of 35% hydrochloric acid was added dropwise to the reaction mixture at from 0° C. to 10° C. and extracted with dichloromethane. The extract was washed with water and brine, dried, and then evaporated. The residue was chromatographed on silica gel using n-hexane and the eluent was distilled to give 58 g of the desired compound as a colorless oil, b.p. 113°–117° C. (22 mmHg).

NMR spectrum δ(CDCl$_3$)ppm: 6.90–7.27(2H, m).

In the same manner as described in Reference 1, the compounds of References 2 and 3 were prepared.

REFERENCE 2

2,3,4-Trifluorophenyl isothiocyanate

A colorless oil, b.p. 70°–93° C. (25 mmHg).
NMR spectrum δ(CDCl$_3$)ppm: 6.73–7.15(2H, m).

REFERENCE 3

3,4-Difluorophenyl isothiocyanate

A colorless oil, b.p. 107°–110° C. (35 mmHg).
NMR spectrum δ(CDCl$_3$)ppm: 6.67–7.33(3H, m).

REFERENCE 4

Ethyl 8-chloro-6,7-difluoro-4-hydroxy-2-(methoxymethylthio)quinoline-3-carboxylate To a solution of 45 g of diethyl malonate in 500 ml of abs. tetrahydrofuran, 11.2 g of 60% sodium hydride oil suspension was added under ice cooling with stirring. After 15 minutes, 57 g of 2-chloro-3,4-difluorophenyl isothiocyanate was added to the reaction mixture at room temperature with stirring. The reaction mixture was stirred for 15 minutes and then 22.5 g of chloromethyl methyl ether was added at the same temperature.

After 15 minutes, the reaction mixture was concentrated in vacuo, and water was added to the residue. The mixture was extracted with chloroform. The extract was washed with water and brine, dried and evaporated to give 115 g of pale yellow oil. The oil was heated at from 170° C. to 175° C. under reduced pressure for 15 minutes. After cooling, the obtained precipitate was washed with ethanol and recrystallized from ethanol to give 60 g of the desired compound as colorless needles, m.p. 105°–108° C.

NMR spectrum $\delta(CDCl_3)$ppm: 1.55(3H, t, J=7 Hz), 3.48(3H, s), 4.56(2H, q, J=7 Hz), 5.54(2H, s), 7.85(1H, dd, J=10, 8 Hz)

In the same manner as described in Reference 4, the compounds of References 5 and 6 were prepared.

REFERENCE 5

Ethyl 6,7,8-trifluoro-4-hydroxy-2-(methoxymethylthio)quinoline-3-carboxylate

Pale yellow needles (EtOH), m.p. 91°–94° C.

NMR spectrum $\delta(DMSO-d_6)$ppm: 1.35(3H, t, J=7 Hz), 3.32(3H, s), 4.38(2H, q, J=7 Hz), 5.44(2H, s), 7.92(1H, ddd, J=10.5, 8, 2 Hz)

REFERENCE 6

Ethyl 6,7-difluoro-4-hydroxy-2-(methoxymethylthio)quinoline-3-carboxylate

Colorless crystals (AcOEt), m.p. 123°–127° C.

NMR spectrum $\delta(CDCl_3)$ppm: 1.54(3H, t, J=7 Hz), 3.46(3H, s), 4.56(2H, q, J=7 Hz), 5.45(2H, s), 7.55(1H, dd, J=11, 7 Hz), 7.91(1H, dd, J=10.5, 8.5 Hz).

REFERENCE 7

Ethyl 8-chloro-6,7-difluoro-4-hydroxy-2-mercaptoquinoline-3-carboxylate

To a solution of 15.7 g of ethyl 8-chloro-6,7-difluoro-4-hydroxy-2-(methoxymethylthio)quinoline-3-carboxylate in 125 ml of 1,4-dioxane, 95 ml of 35% hydrochloric acid was added dropwise at 40° C. with stirring. The mixture was stirred at the same temperature for 1 hour. The reaction mixture was poured into 500 ml of water. The precipitate was collected by filtration and recrystallized from acetonitrile to give 11.2 g of the desired compound as pale yellow needles, m.p. 125°–130° C. (decomp.).

NMR spectrum $\delta(CDCl_3)$ppm: 1.54(3H, t, J=7 Hz), 4.56(2H, q, J=7 Hz), 5.30(2H, s), 7.91(1H, dd, J=10, 8 Hz).

In the same manner as described in Reference 7, the compounds of References 8 and 9 were prepared.

REFERENCE 8

Ethyl 6,7,8-trifluoro-4-hydroxy-2-mercaptoquinoline-3-carboxylate

Yellow crystals (DMF-EtOH), m.p. 188°–190° C. (decomp.).

NMR spectrum $\delta(DMSO-d_6)$ppm: 1.28(3H, t, J=7 Hz), 4.26(2H, q, J=7 Hz), 7.83(1H, ddd, J=11, 7.5, 2.5 Hz).

REFERENCE 9

Ethyl 6,7-difluoro-4-hydroxy-2-mercaptoquinoline-3-carboxylate

Yellow needles (DMF-EtOH), m.p. 201°–203° C. (decomp.).

NMR spectrum $\delta(DMSO-d_6)$ppm: 1.29(3H, t, J=7.5 Hz), 4.27(2H, q, J=7.5 Hz), 7.53(1H, dd, J=11.5, 7.5 Hz), 8.00(1H, dd, J=11, 8.5 Hz).

REFERENCE 10

Ethyl 8-chloro-6,7-difluoro-1-methyl-4-oxo-1H,4H-[1,3]thiazeto[3,2-a]quinoline-3-carboxylate To a suspension of 13.7 g of 1,1-dibromoethane, 5.7 g of potassium iodide and 9.5 g of potassium carbonate in 60 ml of N,N-dimethylformamide, a solution of 11.1 g of ethyl 8-chloro-6,7-difluoro-4-hydroxy-2-mercaptoquinoline-3-carboxylate in 240 ml of N,N-dimethylformamide was added dropwise at from 110° C. to 115° C. during 2 hours with stirring. After stirring for 30 minutes at the same temperature, the reaction mixture was concentrated in vacuo and water was added to the residue. The precipitate was collected by filtration and chromatographed on silica gel using chloroform. The eluent was recrystallized from a mixture of chloroform and diethyl ether to give colorless needles, m.p. 191°–194° C.

NMR spectrum $\delta(CDCl_3)$ppm: 1.41(3H, t, J=7 Hz), 2.27(3H, d, J=6 Hz), 4.39(2H, q, J=7 Hz), 6.33(1H, q, J=6 Hz), 8.22(1H, dd, J=10, 8 Hz).

In the same manner as described in Reference 10, the compounds of References 11 and 12 were prepared.

REFERENCE 11

Ethyl 6,7,8-trifluoro-1-methyl-4-oxo-1H,4H-[1,3]thiazeto[3,2-a]quinoline-3-carboxylate Colorless needles (DMF), m.p. 206°–210° C.

NMR spectrum $\delta(DMSO-d_6)$ppm: 1.27(3H, t, J=7 Hz), 2.06(3H, dd, J=6, 3 Hz), 4.21(2H, q, J=7 Hz), 6.26(1H, qd, J=6, 2 Hz), 7.84(1H, ddd, J=10.5, 7.5, 2.5 Hz).

REFERENCE 12

Ethyl 6,7-difluoro-1-methyl-4-oxo-1H,4H-[1,3]thiazeto[3,2-a]quinoline-3-carboxylate Colorless needles (DMF), m.p. 197°–199° C.

NMR spectrum $\delta(DMSO-d_6)$ppm: 1.27(3H, t, J=7.5 Hz), 2.08(3H, d, J=6.5 Hz), 4.19(2H, q, J=7.5 Hz), 6.12(1H, q, J=6.5 Hz), 7.67(1H, dd, J=11, 6.5 Hz), 7.94(1H, dd, J=11, 8.5 Hz).

REFERENCE 13

Ethyl 6-fluoro-1-methyl-4-oxo-7-(3-trifluoroacetylamino-1-pyrrolidinyl)-1H,4H-[1,3]thiazeto[3,2-a]quinoline-3-carboxylate A mixture of 1.00 g of ethyl 6,7-difluoro-1-methyl-4-oxo-1H,4H-[1,3]thiazeto[3,2-a]quinoline-3-carboxylate, 2.1 g of 3-trifluoroacetylaminopyrrolidine hydrochloride, 1.46 g of 1,8-diazabicyclo[5,4,0]-7-undecene and 20 ml of N,N-dimethylformamide was stirred at room temperature for 72 hours. The reaction mixture was concentrated in vacuo, and, to a suspension of the residue in 20 ml of methanol, 30 ml of water was added. The precipitate was collected by filtration to give 1.22 g of the desired compound, which was recrystallized from a mixture of chloroform and ethanol to give colorless crystals, m.p. 255°–257° C. (decomp.).

NMR spectrum δ(CDCl$_3$)ppm: 1.36(3H, t, J=7 Hz), 2.01(3H, d, J=6 Hz), 2.00–2.45(2H, m), 3.20–4.93(5H, m), 4.31(2H, q, J=7 Hz), 5.49–5.97(2H, m), 7.43, 7.50(total 1H, each d, J=14.5 Hz), 8.80–9.33 (1H, m).

In the same manner as described in Reference 13, the compounds of Reference 14 to 19 were prepared.

REFERENCE 14

Ethyl 6-fluoro-1-methyl-4-oxo-7-((S)-3-trifluoroacetylamino-1-pyrrolidinyl)-1H,4H-[1,3]thiazeto[3,2-a]quinoline-3-carboxylate The desired compound was prepared using (S)-3-trifluoroacetylaminopyrrolidine hydrochloride [[α]$_D^{20}$ −28.6° (c=1, MeOH)].

Pale gray crystals (CHCl$_3$-EtOH), m.p. 259°–261° C. (decomp.).

NMR spectrum δ(DMSO-d$_6$)ppm: 1.25(3H, t, J=7 Hz), 1.87–2.45 (2H, m), 2.04(3H, d, J=6 Hz), 3.36–4.64(5H, m), 4.17(2H, q, J=7 Hz), 6.12(1H, q, J=6 Hz), 6.33(1H, d, J=7.5 Hz), 7.62(1H, d, J=15 Hz), 9.47–9.73(1H, m).

REFERENCE 15

Ethyl 7-[(S)-3-(tert-butoxycarbonylamino)-1-pyrrolidinyl]-6-fluoro-1-methyl-4-oxo-1H,4H-[1,3]thiazeto[3,2-a]quinoline-3-carboxylate The desired compound was prepared using (S)-3-(tert-butoxycarbonylamino)pyrrolidine [[α]$_D^{20}$ −21.6° (c=1, EtOH)].

Colorless prisms (CH$_3$CN), m.p. 242°–245° C. (decomp.).

NMR spectrum δ(DMSO-d$_6$)ppm: 1.25(3H, t, J=7 Hz), 1.40(9H, s), 1.80–2.20(2H, m), 2.04(3H, d, J=6 Hz), 3.10–3.84(5H, m), 4.17(2H, q, J=7 Hz), 6.12(1H, q, J=6 Hz), 6.29(1H, d, J=8 Hz), 7.00(1H, br), 7.60(1H, d, J=15 Hz).

REFERENCE 16

Ethyl 7-[(R)-3-(tert-butoxycarbonylamino)-1-pyrrolidinyl]-6-fluoro-1-methyl-4-oxo-1H,4H-[1,3]thiazeto[3,2-a]quinoline-3-carboxylate The desired compound was prepared using (R)-3-(tert-butoxycarbonylamino)pyrrolidine [[α]$_D^{20}$ +21.4° (c=1, EtOH)].

Pale red needles (CH$_3$CN), m.p. 242°–245° C. (decomp.).

NMR spectrum δ(DMSO-d$_6$)ppm: 1.25(3H, t, J=7 Hz), 1.40(9H, s), 1.80–2.20(2H, m), 2.03(3H, d, J=6 Hz), 3.10–3.85(5H, m), 4.17(2H, q, J=7 Hz), 6.12(1H, q, J=6 Hz), 6.28(1H, d, J=7.5 Hz), 6.98(1H, br), 7.60(1H, d, J=15 Hz).

REFERENCE 17

Ethyl 7-(3-dimethylamino-1-pyrrolidinyl)-6-fluoro-1-methyl-4-oxo-1H,4H-[1,3]thiazeto[3,2-a]quinoline-3-carboxylate The desired compound was prepared using 3-dimethylaminopyrrolidine.

Colorless needles (CH$_3$CN), m.p. 224°–227° C. (decomp.).

NMR spectrum (DMSO-d$_6$)ppm: 1.24(3H, t, J=7 Hz), 1.60–2.00 (2H, m), 2.04(3H, d, J=6 Hz), 2.22(6H, s), 2.70–3.80(5H, m), 4.16(2H, q, J=7 Hz), 6.11(1H, q, J=6 Hz), 6.32(1H, d, J=7.5 Hz), 7.59(1H, d, J=15 Hz).

REFERENCE 18

Ethyl 7-((S)-3-dimethylamino-1-pyrrolidinyl)-6-fluoro-1-methyl-4-oxo-1H,4H-[1,3]thiazeto[3,2-a]quinoline-3-carboxylate The desired compound was prepared using (S)-3-dimethylamino pyrrolidine [[α]$_D^{20}$ −12.9° (c=1, MeOH)].

Colorless crystals (EtOH-Et$_2$O), m.p. 219°–222° C. (decomp.).

NMR spectrum (CDCl$_3$)ppm: 1.38(3H, t, J=7 Hz), 1.72–3.92(7H, m), 2.06, 2.07(total 3H, each d, J=6 Hz), 2.35(6H, s), 4.34(2H, q, J=7 Hz), 5.70–6.00(2H, m), 7.82(1H, dd, J=15, 0.5 Hz).

REFERENCE 19

Ethyl 7-((R)-3-dimethylamino-1-pyrrolidinyl)-6-fluoro-1-methyl-4-oxo-1H,4H-[1,3]thiazeto[3,2-a]quinoline-3-carboxylate The desired compound was prepared using (R)-3-dimethylaminopyrrolidine [[α]$_D^{20}$ +12.8° (c=1, MeOH)].

Colorless crystals (EtOH-Et$_2$O), m.p. 223°–226° C. (decomp.).

NMR spectrum δ(CDCl$_3$)ppm: 1.39(3H, t, J=7 Hz), 1.84–3.88(7H, m), 2.10(3H, d, J=6.5 Hz), 2.40(6H, s), 4.35(2H, q, J=7 Hz), 5.72–6.04(2H, m), 7.86(1H, d, J=14.5 Hz).

EXAMPLE 1

Ethyl 8-chloro-6-fluoro-1-methyl-4-oxo-7((S)-trifluoroacetylamino-1-pyrrolidinyl)-1H,4H-[1,3]thiazeto[3,2-a]quinoline-3-carboxylate To a suspension of 3.81 g of ethyl 6-fluoro-1-methyl-4-oxo-7-((S)-3-trifluoroacetylamino-1-pyrrolidinyl)-1H,4H-[1,3]thiazeto[3,2-a]quinoline-3-carboxylate in 150 ml of dichloromethane, 0.72 ml of sulfuryl chloride was added dropwise at room temperature with stirring. After 10 minutes, the reaction mixture was washed with water four times, dried and evaporated. The residue was chromatographed on silica gel using chloroform-methanol (30:1) as an eluent to give 2.77 g of the desired compound, which was recrystallized from a mixture of ethyl acetate and diisopropyl ether to give pale yellow crystals, m.p. 153°–156° C.

IR spectrum ν(KBr) cm$^{-1}$: 1710, 1602

NMR spectrum δ(CDCl$_3$)ppm: 1.40(3H, t, J=7 Hz), 1.88–2.60(2H, m), 2.21, 2.22(total 3H, each d, J=6 Hz), 3.16–4.82(5H, m), 4.36, 4.37 (total 3H, each q, J=7 Hz), 6.34, 6.35(total 1H, each q, J=6 Hz), 7.00–7.52(1H, m), 7.90, 7.97(total 1H, each d, J=13 Hz).

The product obtained was a mixture of diastereoisomers containing isomer A (retetion time: 15.4 min.) and isomer B (retention time: 17.5 min.) in the ratio of about 53:47 analyzed under the following HPLC conditions:
COLUMN: SUMIPAX OA-3100 φ4.6 mm×250 mm
Carrier: MeOH
Flow rate: 0.5 ml/min.
Detector: UV spectrometer (287 nm)

EXAMPLE 2

Ethyl 8-chloro-6-fluoro-1-methyl-4-oxo-7-((S)-3-trifluoroacetylamino-1-pyrrolidinyl)-1H,4H-[1,3]thiazeto[3,2-a]quinoline-3-carboxylate To a solution of 1.50 g of ethyl 6-fluoro-1-methyl-4-oxo-7-((S)-3-trifluoroacetylamino-1-pyrrolidinyl)-1H,4H-[1,3]thiazeto[3,2-a]quinoline-3-carboxylate in 4.0 ml of chlorosulfonic acid, a trace of iodine was added, and the mixture was bubbled with chlorine gas for 1 hour under ice cooling with stirring. The reaction mixture was poured into ice water and was extracted with chloroform. The extract was washed with aqueous potassium carbonate and water, dried and evaporated. The residue was chromatographed on silica gel using chloroform-methanol (50:1) as an eluent to give 1.61 g of the desired compound, which was recrystallized from a mixture of ethyl acetate and diisopropyl ether. The obtained crystals were consistent with that of Example 1.

In the same manner as described in Examples 1 and 2, the compounds of Example 3 to 8 were prepared.

EXAMPLE 3

Ethyl 8-chloro-6-fluoro-1-methyl-4-oxo-7-(3-trifluoroacetylamino-1-pyrrolidinyl)-1H,4H-[1,3]thiazeto[3,2-a]quinoline-3-carboxylate Colorless prisms (AcOEt-iso-Pr$_2$O), m.p. 185°–188° C.
IR spectrum $\nu$(KBr)cm$^{-1}$: 1710, 1604
NMR spectrum: $\delta$(CDCl$_3$) ppm: 1.40(3H, t, J=7 Hz), 1.90–2.70 (2H, m) 2.23 (3H, d, J=6 Hz), 3.18–4.82(5H, m), 4.38(2H, q, J=7 Hz), 6.36(1H, q, J=6 Hz), 6.80–7.40(1H, br s), 7.97, 8.01(total 1H, each d, J=13 Hz).

EXAMPLE 4

Ethyl 7-[(S)-3-(tert-butoxycarbonylamino)-1-pyrrolidinyl]-8-chloro-6-fluoro-1-methyl-4-oxo-1H,4H-[1,3]thiazeto[3,2-a]quinoline-3-carboxyate Colorless needles (CH$_3$CN), m.p. 115°–118° C.
IR spectrum $\nu$(KBr)cm$^{-1}$: 1716, 1602
NMR spectrum $\delta$(DMSO-d$_6$) ppm: 1.26(3H, t, J=7 Hz), 1.40(9H, s), 1.58–2.44(2H, m), 2.11(3H,d, J=6 Hz), 3.14–3.99 (5H, m), 4.20(2H, q, J=7 Hz), 6.46(1H, q, J=6Hz), 6.90–7.11(1H, br), 7.73(1H, d, J=14 Hz).
Specific rotation $[\alpha]_D^{20}$+240.6° (c=0.1, CHCl$_3$)

EXAMPLE 5

Ethyl [(R)-3-(tert-butoxycarbonylamino)-1-pyrrolidinyl]-8-chloro-6-fluoro-1-methyl-4-oxo-1H,4H-[1,3]thiazeto[3,2-a]quinoline-3-carboxylate Colorless crystals (AcOEt-Et$_2$O), m.p. 174°–177° C. (decomp.).
IR spectrum $\nu$(KBr)cm$^{-1}$: 1710, 1600
NMR spectrum $\delta$(CDCl$_3$) ppm: 1.41 (3H, t, J=7 Hz), 1.46, 1.47 total 9H, each s), 1.60–2.55(2H, m), 2.21(3H, d, J=6 Hz), 3.02–4.93(5H,m), 4.38(2H, q, J=7 Hz), 6.36(1H, q, J=6 Hz), 8.01(1H, d, J=13 Hz).

EXAMPLE 6

Ethyl 8-chloro-7-(3-dimethylamino-1-pyrrolidinyl)-6-fluoro-1-methyl-4-oxo-1H,4H-[1,3]thiazeto[3,2-a]quinoline-3-carboxylate Pale yellow crystals (AcOEt-iso-Pr$_2$O), m.p. 128°–129.4° C.
IR spectrum $\nu$(KBr)cm$^{-1}$: 1732, 1678, 1628, 1600
NMR spectrum $\delta$(CDCl$_3$) ppm: 1.40 (3H, t, J=7 Hz), 1.70–4.20(7H, m), 2.20, 2.22(total 3H, each d, J=6 Hz), 2.38, 2.39(total 3H, each s), 4.38(2H, q, J=7 Hz), 6.35(1H, q, J=6 Hz), 8.01, 8.03(total 1H, each d, J=13.5 Hz)

EXAMPLE 7

Ethyl 8-chloro-7-((S)-3-dimethylamino-1-pyrrolidinyl)-6-fluoro-1-methyl-4-oxo-1H,4H-[1,3]thiazeto[3,2-a]quinoline-3-carboxylate Pale brown needles (AcOEt), m.p. 131°–133° C.
IR spectrum $\nu$(KBr)cm$^{-1}$: 1738, 1674, 1628, 1602
NMR spectrum $\delta$(CDCl$_3$) ppm: 1.41 (3H, t, J=7 Hz), 1.70–4.20(7H, m), 2.20, 2.22(total 3H, each d, J=6 Hz), 2.36(6H, s), 4.38(2H, q, J=7 Hz), 6.35(1H, q, J=6 Hz), 7.98, 8.01(total 1H, each d, J=13.5 Hz)

EXAMPLE 8

Ethyl 8-chloro-7-((R)-3-dimethylamino-1-pyrrolidinyl)-6-fluoro-1-methyl-4-oxo-1H,4H-[1,3]thiazeto[3,2-a]quinoline-3-carboxylate Pale brown needles (AcOEt), m.p. 132°–134° C.
IR spectrum $\nu$(KBr)cm$^{-1}$: 1738, 1674, 1628, 1602
NMR spectrum $\delta$(CDCl$_3$) ppm: 1.41 (3H, t, J=7 Hz), 1.70–4.12(7H, m), 2.20, 2.22(total 3H, each d, J=6 Hz), 2.34(6H, s), 4.38(2H, q, J=7 Hz), 6.35(1H, q, J=6 Hz), 7.98, 8.00(total 1H, each d, J=13.5 Hz)

EXAMPLE 9

Ethyl 6,8-difluoro-1-methyl-4-oxo-7-((S)-3-trifluoroacetylamino-1-pyrrolidinyl)-1H,4H-[1,3]thiazeto[3,2-a]quinoline-3-carboxylate A mixture of 1.34 g of ethyl 6,7,8-trifluoro-1-methyl-4-oxo-1H,4H-[1,3]thiazeto[3,2-a]quinoline-3-carboxylate, 2.66 g of (S)-3-trifluoroacetylaminopyrrolidine hydrochloride [[$\alpha$]$_D^{20}$ −28.6° (c=1, MeOH)], 1.80 g of 1.8-diazabicyclo[5,4,0]-7-undecene and 30 ml of N,N-dimethylformamide was stirred at room temperature for 5 hours. The reaction mixture was concentrated in vacuo, and water was added to the residue. The precipitate was collected by filtration and was chromatographed on silica gel using chloroform-methanol (8:2) to give the desired compound, which was recrystallized from methanol to give 0.80 g of pale yellow needles, m.p. 219°–224° C.

IR spectrum $\nu$(KBr)cm$^{-1}$: 1722, 1602

NMR spectrum $\delta$(DMSO-d$_6$)ppm: 1.26 (3H, t, J=7 Hz), 1.84–2.40 (2H, m), 2.03(3H, dd, J=6.3 Hz), 3.46–4.60(5H, m), 4.18(2H, q, J=7 Hz), 6.14(1H, dd, J=6, 2.5 Hz), 7.48(1H, dd, 14.5, 1.5 Hz), 9.42–9.68(1H, br).

Specific rotation $[\alpha]_D^{20}$ −121.5° (c=0.1, CHCl$_3$)

In the same manner as described in Example 9, the compounds of Example 10 to 22 were prepared.

EXAMPLE 10

Ethyl 6,8-difluoro-1-methyl-4-oxo-7-(3-trifluoroacetylamino-1-pyrrolidinyl)-1H,4H-[1,3]thiazeto[3,2-a]quinoline-3-carboxylate Colorless crystals (CHCl$_3$-AcOEt), m.p. 235°–237° C.

IR spectrum $\nu$(KBr)cm$^{-1}$: 1716, 1604

NMR spectrum $\delta$(CDCl$_3$)ppm: 1.35, 1.37(total 3H, each t, J=7 Hz), 2.02(3H, dd, J=6, 2.5 Hz), 1.91–2.51(2H, m), 3.41–4.90(5H, m), 4.24, 4.30(total 2H, each q, J=7 Hz), 5.65–6.10(1H, m), 7.20–7.57(1H, m), 8.75–9.33(1H, m).

EXAMPLE 11

Ethyl 7-[(S)-3-(tert-butoxycarbonylamino)-1-pyrrolidinyl]-6,8-difluoro-1-methyl-4-oxo-1H,4H-[1,3]thiazeto[3,2-a]quinoline-3-carboxylate The desired compound was prepared using (S)-3-(tert-butoxycarbonylamino)pyrrolidine $[[\alpha]_D^{20}$ −21.6° (c=1, EtOH)].

Pale yellow crystals (CHCl$_3$-Et$_2$O), m.p. 179°–180° C.

IR spectrum $\nu$(KBr)cm$^{-1}$: 1714, 1610

NMR spectrum $\delta$(CDCl$_3$)ppm: 1.39(3H, t, J=7 Hz), 1.46(9H, s), 1.70–2.32(2H, m), 2.09(3H, dd, J=6, 3 Hz), 3.40–4.40(5H, m), 4.36(2H, q, J=7 Hz), 4.90–5.20(1H, br), 5.80–6.10(1H, m), 7.69(1H, dd, J=14.5, 2 Hz).

Specific rotation $[\alpha]_D^{20}$ +81.7° (c=0.1, CHCl$_3$)

EXAMPLE 12

Ethyl 7-[(R)-3-(tert-butoxycarbonylamino)-1-pyrrolidinyl]-6,8-difluoro-1-methyl-4-oxo-1H,4H-[1,3]thiazeto[3,2-a]quinoline-3-carboxylate The desired compound was prepared using (R)-3-(tert-butoxycarbonylamino)pyrrolidine $[[\alpha]_D^{20}$ +21.4° (c=1, EtOH)].

Pale yellow crystals (CHCl$_3$-Et$_2$O), m.p. 174°–176° C.

IR spectrum $\nu$(KBr)cm$^{-1}$: 1714, 1608

NMR spectrum $\delta$(CDCl$_3$)ppm: 1.39(3H, t, J=7 Hz), 1.46(9H, s), 1.76–2.34(2H, m), 2.10(3H, dd, J=6, 3 Hz), 3.40–4.40(5H, m), 4.36(2H, q, J=7 Hz), 4.80–5.10(1H, br), 5.80–6.10(1H, m), 7.73(1H, dd, J=14.5, 2 Hz).

EXAMPLE 13

Ethyl 7-(3-dimethylamino-1-pyrrolidinyl)-6,8-difluoro-1-methyl-4-oxo-1H,4H-[1,3]thiazeto[3,2-a]quinoline-3-carboxylate Pale yellow crystals (AcOEt), m.p. 174°–178° C.

IR spectrum $\nu$(KBr)cm$^{-1}$: 1672, 1636, 1608

NMR spectrum $\delta$(DMSO-d$_6$)ppm: 1.25(3H, t, J=7 Hz), 1.60–3.85(7H, m), 2.02(3H, dd, J=6, 3 Hz), 2.21(6H, s), 4.18(2H, q, J=7 Hz), 6.14(1H, qd, J=6, 2.5 Hz), 7.47(1H, dd, J=14.5, 2 Hz).

EXAMPLE 14

Ethyl 7-((S)-3-dimethylamino-1-pyrrolidinyl)-6,8-difluoro-1-methyl-4-oxo-1H,4H-[1,3]thiazeto[3,2-a]quinoline-3-carboxylate The desired compound was prepared using (S)-3-dimethylamino pyrrolidine $[[\alpha]_D^{20}$ −12.9° (c=1, MeOH)].

Pale brown crystals (AcOEt), m.p. 163°–164° C.

IR spectrum $\nu$(KBr)cm$^{-1}$: 1668, 1636, 1610

NMR spectrum $\delta$(DMSO-d$_6$)ppm: 1.26(3H, t, J=7 Hz), 1.60–3.90(7H, m), 2.02(3H, dd, J=6, 3 Hz), 2.20(6H, s), 4.18(2H, q, J=7 Hz), 6.13(1H, qd, J=6, 2 Hz), 7.45(1H, dd, J=14.5, 2 Hz).

EXAMPLE 15

Ethyl 7-((R)-3-dimethylamino-1-pyrrolidinyl)-6,8-difluoro-1-methyl-4-oxo-1H,4H-[1,3]thiazeto[3,2-a]quinoline-3-carboxylate The desired compound was prepared using (R)-3-dimethylamino pyrrolidine $[[\alpha]_D^{20}$ +12.8° (c=1, MeOH)].

Pale brown crystals (AcOEt), m.p. 165°–168° C.

IR spectrum $\nu$(KBr)cm$^{-1}$: 1668, 1636, 1612

NMR spectrum $\delta$(DMSO-d$_6$)ppm: 1.25(3H, t, J=7 Hz), 1.60–3.97(7H, m), 2.02(3H, dd, J=6, 3 Hz), 2.20(6H, s), 4.18(2H, q, J=7 Hz), 6.15(1H, qd, J=6, 2 Hz), 7.48(1H, dd, J=14.5, 2 Hz).

EXAMPLE 16

Ethyl 8-chloro-6-fluoro-1-methyl-4-oxo-7-(3-trifluoroacetylamino-1-pyrrolidinyl)-1H,4H-[1,3]thiazeto[3,2-a]quinoline-3-carboxylate The obtained compound was consistent with that of Example 3.

EXAMPLE 17

Ethyl 8-chloro-6-fluoro-1-methyl-4-oxo-7-((S)-3-trifluoroacetylamino-1-pyrrolidinyl)-1H,4H-[1,3]thiazeto[3,2-a]quinoline-3-carboxylate The desired compound was prepared using (S)-3-trifluoroacetylaminopyrrolidine hydrochloride $[[\alpha]_D^{20}$ −28.6° (C=1, MeOH)].

The obtained compound was consistent with that of Example 1.

EXAMPLE 18

Ethyl 7-[(S)-3-(tert-butoxycarbonylamino)-1-pyrrolidinyl]-8-chloro-6-fluoro-1-methyl-4-oxo-1H,4H-[1,3]thiazeto[3,2-a]quinoline-3-carboxylate The desired compound was prepared using (S)-3-(tert-butoxycarbonylamino)pyrrolidine [[α]$_D^{20}$−21.6° (c=1, EtOH)].

The obtained compound was consistent with that of Example 4.

EXAMPLE 19

Ethyl 7-[(R)-3-(tert-butoxycarbonylamino)-1-pyrrolidinyl]-8-chloro-6-fluoro-1-methyl-4-oxo-1H,4H-[1,3]thiazeto[3,2-a]quinoline-3-carboxylate The desired compound was prepared using (R)-3-(tert-butoxycarbonylamino)pyrrolidine [[α]$_D^{20}$+21.4° (c=1, EtOH)].

The obtained compound was consistent with that of Example 5.

EXAMPLE 20

Ethyl 8-chloro-7-(3-dimethylamino-1-pyrrolidinyl)-6-fluoro-1-methyl-4-oxo-1H,4H-[1,3]thiazeto[3,2-a]quinoline-3-carboxylate The obtained compound was consistent with that of Example 6.

EXAMPLE 21

Ethyl 8-chloro-7-((S)-3-dimethylamino-1-pyrrolidinyl)-6-fluoro-1-methyl-4-oxo-1H,4H-[1,3]thiazeto[3,2-a]quinoline-3-carboxylate The desired compound was prepared using (S)-3-dimethylamino pyrrolidine [[α]$_D^{20}$−12.9° (c=1, MeOH)].

The obtained compound was consistent with that of Example 7.

EXAMPLE 22

Ethyl 8-chloro-7-((R)-3-dimethylamino-1-pyrrolidinyl)-6-fluoro-1-methyl-4-oxo-1H,4H-[1,3]thiazeto[3,2-a]quinoline-3-carboxylate The desired compound was prepared using (R)-3-dimethylamino pyrrolidine [[α]$_D^{20}$+12.8° (c=1, MeOH)].

The obtained compound was consistent with that of Example 8.

EXAMPLE 23

Ethyl 7-((S)-3-amino-1-pyrrolidinyl)-6,8-difluoro-1-methyl-4-oxo-1H,4H-[1,3]thiazeto[3,2-a]quinoline-3-carboxylate A mixture of 0.40 g of ethyl 7-[(S)-3-(tert-butoxycabonyl amino)-1-pyrrolidinyl)-6,8-difluoro-1-methyl-4-oxo-1H,4H-[1,3]thiazeto[3,2-a]quinoline-3-carboxylate and 4.0 ml of 35% hydrochloric acid was heated at 80° C. for 10 minutes with stirring. The reaction mixture was neutralized with 20% aqueous sodium hydroxide. The precipitate was collected by filtration to give 0.29 g of the desired compound, which was recrystallized from ethanol to give pale brown crystals, m.p. 225°–230° C. (decomp.).

IR spectrum ν(KBr)cm$^{-1}$: 1716, 1634

NMR spectrum δ(CD$_3$OD)ppm: 1.35, 1.38(total 3H, each t, J=7 Hz), 1.93–2.48(5H, m), 3.50–4.48(7H, m), 5.92–6.19(1H, m), 7.18–7.52(1H, m).

Specific rotation [α]$_D^{20}$−140.9° (c=0.1, MeOH)

In the same manner as described in Example 23, the compounds of Example 24 to 26 were prepared.

EXAMPLE 24

Ethyl 7-((R)-3-amino-1-pyrrolidinyl)-6,8-difluoro-1-methyl-4-oxo-1H,4H-[1,3]thiazeto[3,2-a]quinoline-3-carboxylate Pale gray prisms (EtOH), m.p. 218°–223° C. (decomp.).

IR spectrum ν(KBr)cm$^{-1}$: 1712, 1634

NMR spectrum δ(DMSO-d$_6$)ppm: 1.26(3H, t, J=7 Hz), 1.87–2.38 (2H, m), 2.04(3H, dd, J=6, 3 Hz), 3.30–4.10(5H, m), 4.19(2H, q, J=7 Hz), 6.00–6.30(1H, m), 7.50(1H, dd, J=14.5, 1.5 Hz).

EXAMPLE 25

Ethyl 7-((S)-3-amino-1-pyrrolidinyl)-8chloro-6-fluoro-1-methyl-4-oxo-1H,4H-[1,3]thiazeto[3,2-a]quinoline-3-carboxylate Pale yellow crystals (CHCl$_3$-Et$_2$O), m.p. 142°–147° C. (decomp.).

IR spectrum ν(KBr)cm$^{-1}$: 1724, 1602

NMR spectrum δ(DMSO-d$_6$)ppm: 1.26(3H, t, J=7 Hz), 1.60–2.00 (2H, m), 2.11(3H, d, J=6 Hz), 3.00–4.00(5H, m), 4.20(2H, q, J=7 Hz), 6.45(1H, q, J=6 Hz), 7.73(1H, d, J=14 Hz).

Specific rotation [α]$_D^{20}$−21.1° (c=1, DMF)

The product obtained was a mixture of diastereoisomers containing isomer A (retetion time: 10.5 min.) and isomer B (retetion time: 11.7 min.) in the ratio of about 1:1 analyzed under the following HPLC conditions:

COLUMN: TSK gel ODS-80T$_M$ ϕ4.6 mm×150 mm
Carrier: methanol: pH2.5 phosphate buffer (3:4) containing 0.05M 1-pentanesulfonic acid sodium salt
Flow rate: 1.0 ml/min.
Detector: UV spectrometer (287 nm)

EXAMPLE 26

Ethyl 7-((R)-3-amino-1-pyrrolidinyl)-8-chloro-6-fluoro-1-methyl-4-oxo-1H,4H-[1,3]thiazeto[3,2-a]quinoline-3-carboxylate Pale yellow crystals (CHCl$_3$), m.p. 126°–131° C. (decomp.).

IR spectrum ν(KBr)cm$^{-1}$: 1728, 1602

NMR spectrum δ(DMSO-d$_6$)ppm: 1.26(3H, t, J=7 Hz), 1.60–2.03 (2H, m), 2.11(3H, d, J=6 Hz), 2.80–4.01(7H, m), 4.20(2H, q, J=7 Hz), 6.44(1H, q, J=6 Hz), 7.71(1H, d, J=14 Hz).

EXAMPLE 27

7-((S)-3-Amino-1-pyrrolidinyl)-6,8-difluoro-1-methyl-4-oxo-1H,4H-[1,3]thiazeto[3,2-a]quinoline-3-carboxylic acid A mixture of 0.96 g of ethyl 7-((S)-3-amino-1-pyrrolidinyl)-6,8-difluoro-1-methyl-4-oxo-1H,4H-[1,3]thiazeto[3,2-a]quinoline-3-carboxylate, 0.80 g of 85% potassium hydroxide, 3.0 ml of tert-butanol and 9.0 ml of water was heated at 50° C. for 2 hours with stirring.

After cooling, the reaction mixture was neutralized with 10% hydrochloric acid. The precipitate was collected by filtration to give 0.75 g of the desired compound, which was recrystallized from a mixture of water and methanol to give pale brown crystals, m.p. 220°–225° C. (decomp.).

IR spectrum ν(KBr)cm$^{-1}$: 1606

NMR spectrum δ(DMSO-d$_6$)ppm: 1.50–2.24(2H, m), 2.09(3H, dd, J=6.5, 3 Hz), 3.20–4.08(5H, m), 6.26–6.54(1H, m), 7.59(1H, dd, J=14.5, 2 Hz).

The product obtained was a mixture of diastereoisomers containing isomer A (retetion time: 14.0 min.) and isomer B (retetion time: 16.6 min.) in the ratio of about 51:49 analyzed under the following HPLC conditions:

COLUMN: TSK gel ODS-80T$_M$ φ4.6 mm×150 mm
Carrier: Aqueous solution containing 6 mM L-isoleucine and 3 mM CuSO$_4$: MeOH (4:1)
Flow rate: 1 ml/min.
Detector: UV spectrometer (287 nm)

In the same manner as described in Example 27, the compounds of Example 28 to 30 were prepared.

EXAMPLE 28

7-((R)-3-Amino-1-pyrrolidinyl)-6,8-difluoro-1-methyl-4-oxo-1H,4H-[1,3]thiazeto[3,2-a]quinoline-3-carboxylic acid The desired compound was prepared using the compound of Example 24.

Pale gray crystals (H$_2$O-MeOH), m.p. 220°–225° C. (decomp.).

IR spectrum ν(KBr)cm$^{-1}$: 1602

NMR spectrum δ(DMSO-d$_6$)ppm: 1.50–2.37(2H, m), 2.09(3H, dd, J=6, 3.5 Hz), 3.24–4.10(5H, m), 6.20–6.52(1H, m), 7.54(1H, dd, J=14.5, 1.5 Hz).

EXAMPLE 29

7-((S)-3-Amino-1-pyrrolidinyl)-8-chloro-6-fluoro-1-methyl-4-oxo-1H,4H-[1,3]thiazeto[3,2-a]quinoline-3-carboxylic acid The desired compound was prepared using the compound of Example 25.

Yellow crystals (H$_2$O), m.p. >300° C.
IR spectrum ν(KBr)cm$^{-1}$: 1598

NMR spectrum δ(DMSO-d$_6$)ppm: 1.60–2.05(2H, m), 2.17(3H, d, J=6 Hz), 3.01–4.98(7H, m), 6.66(1H, q, J=6 Hz), 7.78(1H, d, J=14 Hz).

Specific rotation [α]$_D^{20}$+52.0° (c=0.1, 0.1 NNaOH)

The product obtained was a mixture of diastereoisomers containing isomer A (retetion time: 14.2 min.) and isomer B (retetion time: 16.0 min.) in the ratio of about 59:41 analyzed under the following HPLC conditions:

COLUMN: TSK gel ODS-80T$_M$ φ4.6 mm×150 mm
Carrier: Acetonitrile: pH2.5 phosphate buffer (1:4) containing 0.05M 1-Pentanesulfonic acid Sodium salt
Flow rate: 1.0 ml/min.
Detector: UV spectrometer (287 nm)

EXAMPLE 30

7-((R)-3-Amino-1-pyrrolidinyl)-8-chloro-6-fluoro-1-methyl-4-oxo-1H,4H-[1,3]thiazeto[3,2-a]quinoline-3-carboxylic acid The desired compound was prepared using the compound of Example 26.

Yellow crystals (H$_2$O), m.p. >300° C.
IR spectrum ν(KBr)cm$^{-1}$: 1598

NMR spectrum δ(DMSO-d$_6$)ppm: 1.60–2.01(2H, m), 2.16(3H, d, J=6 Hz), 2.98–4.82(7H, m), 6.66(1H, q, J=6 Hz), 7.78(1H, d, J=14 Hz).

EXAMPLE 31

7-((S)-3-Amino-1-pyrrolidinyl)-8-chloro-6-fluoro-1-methyl-4-oxo-1H,4H-[1,3]thiazeto[3,2-a]quinoline-3-carboxylic acid A mixture of 1.90 g of ethyl 8-chloro-6-fluoro-1-methyl-4-oxo-7-((S)-3-trifluoroacetylamino-1-pyrrolidinyl)-1H,4H-[1,3]-thiazeto[3,2-a]quinoline-3-carboxylate, 1.23 g of 85% potassium hydroxide, 6.0 ml of tert-butanol and 12 ml of water was stirred at room temperature for 5 hours. The reaction mixture was neutralized with aqueous acetic acid. The precipitate was collected by filtration and recrystallized from water to give 0.51 g of yellow crystals, which were consistent with that of Example 29.

In the same manner as described in Example 31, the compounds of Example 32 to 34 were prepared.

EXAMPLE 32

7-((S)-3-Amino-1-pyrrolidinyl)-6,8-difluoro-1-methyl-4-oxo-1H,4H-[1,3]thiazeto[3,2-a]quinoline-3-carboxylic acid The desired compound was prepared using the compound of Example 9.

The obtained compound was consistent with that of Example 27.

EXAMPLE 33

7-(3-amino-1-pyrrolidinyl)-6,8-difluoro-1-methyl-4-oxo-1H,4H-[1,3] thiazeto[3,2-a]quinoline-3-carboxylic acid The desired compound was prepared using the compound of Example 10.

Pale yellow crystals (H$_2$O-MeOH) m.p. 205°–210° C. (decomp.).

IR spectrum ν(KBr)cm$^{-1}$: 1602

NMR spectrum δ(DMSO-d$_6$)ppm: 1.10–2.30(2H, m), 2.09(3H, dd, J=6, 3 Hz), 2.72–4.13(5H, m), 6.25–6.51(1H, m), 7.58(1H, dd, J=14.5, 2 Hz).

EXAMPLE 34

7-(3-Amino-1-pyrrolidinyl)-8-chloro-6-fluoro-1-methyl-4-oxo-1H,4H-[1,3]thiazeto[3,2-a]quinoline-3-carboxylic acid The desired compound was prepared using the compound of Example 3.

Pale yellowish brown crystals (H$_2$O), m.p. >300° C.
IR spectrum ν(KBr)cm$^{-1}$: 1710, 1598

NMR spectrum δ(DMSO-d$_6$)ppm: 1.60–2.00(2H, m), 2.17(3H, d, J=6 Hz), 3.00–4.40(5H, m), 6.68(1H, q, J=6 Hz), 7.80(1H, d, J=14 Hz).

EXAMPLE 35

8-Chloro-7-((S)-3-dimethylamino-1-pyrrolidinyl)-6-fluoro-1-methyl-4-oxo-1H,4H-[1,3]thiazeto[3,2-a]quinoline-3-carboxylic acid A mixture of 0.44 g of ethyl 8-chloro-7-((S)-3-dimethylamino-1-pyrrolidinyl)-6-fluoro-1-methyl-4-oxo-1H,4H-[1,3]thiazeto[3,2-a]quinoline-3-carboxylate, 0.33 g of 85% potassium hydroxide, 2.0 ml of tert-butanol and 6.0 ml of water was heated at 60° C. for 1 hour with stirring. After cooling, the reaction mixture was neutralized with 10% hydrochloric acid, and evaporated. To the residue, water was added and the residue was extracted with chloroform. The extract was dried and acidified with ethanolic hydrochloride. The solution was evaporated and to the residue was added small amount of methanol. The precipitate was collected by filtration and dissolved with water. The solution was neutralized with 10% aqueous sodium hydroxide and extracted with chloroform. The extract was dried, evaporated and recrystallized from a mixture of chloroform and iso-propanol to give 0.25 g of the desired compound as pale yellow crystals, m.p. 161°–162° C.

IR spectrum $\nu$(KBr)cm$^{-1}$: 1716, 1620

NMR spectrum $\delta$(CDCl$_3$)ppm: 1.52–4.24(7H, m), 2.26, 2.29 (total 3H, each d, J=6 Hz), 2.34(6H, s), 6.51(1H, q, J=6 Hz), 7.88, 7.91(total 1H, each d, J=13.5 Hz).

In the same manner as described in Example 35, the compounds of Example 36 to 40 were prepared.

EXAMPLE 36

7-(3-Dimethylamino-1-pyrrolidinyl)-6,8-difluoro-1-methyl-4-oxo-1H,4H-[1,3]thiazeto[3,2-a]quinoline-3-carboxylic acid Pale yellow crystals (H$_2$O), m.p. 227°–232° C. (decomp.).

IR spectrum $\nu$(KBr)cm$^{-1}$: 1712, 1634, 1596

NMR spectrum $\delta$(CF$_3$COOD)ppm: 2.18–4.56(10H, m), 3.21(6H, s), 6.43–6.78(1H, m), 7.97(1H, d, J=13 Hz).

EXAMPLE 37

7-((S)-3-Dimethylamino-1-pyrrolidinyl)-6,8-difluoro-1-methyl-4-oxo-1H,4H-[1,3]thiazeto[3,2-a]quinoline-3-carboxylic acid Pale yellow crystals (H$_2$O), m.p. 215°–220° C. (decomp.).

IR spectrum $\nu$(KBr)cm$^{-1}$: 1716, 1632, 1600

NMR spectrum $\delta$(DMSO-d$_6$)ppm: 1.60–4.00(7H, m), 2.09(3H, dd, J=6, 3 Hz), 2.21(6H, s), 6.08–6.76(1H, m), 7.58(1H, dd, J=14.5, 2 Hz).

EXAMPLE 38

7-((R)-3-Dimethylamino-1-pyrrolidinyl)-6,8-difluoro-1-methyl-4-oxo-1H,4H-[1,3]thiazeto[3,2-a]quinoline-3-carboxylic acid Pale yellow crystals (H$_2$O), m.p. 213°–218° C. (decomp.). IR spectrum $\nu$ (KBr)cm$^{-1}$: 1716, 1632, 1600 NMR spectrum $\delta$ (DMSO-d$_6$)ppm: 1.59–3.93(7H, m), 2.09(3H, dd, J=6.5, 3 Hz), 2.21(6H, s), 6.38(1H, dd, J=6.5, 2 Hz), 7.57(1H, dd, J=14.5, 2 Hz)

EXAMPLE 39

8-Chloro-7-(3-dimethylamino-1-pyrrolidinyl)-6-fluoro-1-methyl-4-oxo-1H,4H-[1,3]thiazeto[3,2-a]quinoline-3-carboxylic acid Colorless crystals (CH$_3$CN), m.p. 202°–205° C. (decomp.). IR spectrum $\nu$ (KBr)cm$^{-1}$: 1706, 1616 NMR spectrum $\delta$ (DMSO-d$_6$)ppm: 1.60–2.00(2H, m), 2.18(3H, d, J=6 Hz), 2.22(6H, s), 2.70–3.00(1H, m), 3.30–4.00(4H, m), 6.67(1H, q, J=6 Hz), 7.77(1H, d, J=14 Hz).

EXAMPLE 40

8-Chloro-7-((R)-3-dimethylamino-1-pyrrolidinyl)-6-fluoro-1-methyl-4-oxo-1H,4H-[1,3]thiazeto[3,2-a]quinoline-3-carboxylic acid Pale yellow crystals (CHCl$_3$-iso-PrOH), m.p. 160°–162° C. IR spectrum $\nu$ (KBr)cm$^{-1}$: 1716, 1620 NMR spectrum $\delta$ (CDCl$_3$)ppm: 1.50–4.28(7H, m), 2.26, 2.29 (total 3H, each d, J=6 Hz), 2.34(6H, s), 6.53(1H, q, J=6 Hz), 7.87, 7.90(total 1H, each d, J=13.5 Hz).

EXAMPLE 41

7-(3-Amino-1-pyrrolidinyl)-8-chloro-6-fluoro-1-methyl-4-oxo-1H,4H-[1,3]thiazeto[3,2-a]quinoline-3-carboxylic acid To a solution of 1.80 g of 7-(3-amino-1-pyrrolidinyl)-6-fluoro-1-methyl-4-oxo-1H,4H-[1,3]thiazeto[3,2-a]quinoline-3-carboxylic acid in 10 ml of chlorosulfonic acid, a trace of iodine was added, and the mixture was bubbled with chlorine gas for 3.5 hours under ice-cooling with stirring. The reaction mixture was poured into ice-water and neutralized to pH 8 with 10% aqueous sodium hydroxide. The precipitate obtained was collected by filtration and converted to the methanesulfonate. The salt was dissolved into water and filtered. The filtrate was neutralized to pH 8 with 10% aqueous sodium hydroxide. The precipitate was collected by filtration to give 1.50 g of pale yellowish-brown crystals.

The obtained compound was consistent with that of Example 34.

EXAMPLE 42

8-chloro-7-(3-dimethylamino-1-pyrrolidinyl)-6-fluoro-1-methyl-4-oxo-1H,4H-[1,3]thiazeto[3,2-a]quinoline-3-carboxylic acid To a solution of 0.60 g of 7-(3-dimethylamino-1-pyrrodinyl)-6-fluoro-1-methyl-4-oxo-1H,4H-[1,3]thiazeto[3,2-a]quinoline-3-carboxylic acid in 2 ml of chlorosulfonic acid, a trace of iodine was added and the mixture was bubbled with chlorine gas for 2.5 hours under ice-cooling with stirring. The reaction mixture was poured into ice-water, neutralized to pH 8 with 10% aqueous sodium hydroxide and extracted with chloroform. The extract was dried and evaporated. Ether was added to the residue and the precipitate was collected by filtration, which was recrystallized from acetonitrile to give 0.10 g of colorless crystals.

The obtained compound was consistent with that of Example 39.

EXAMPLE 43

Ethyl 7-((R)-3-amino-1-pyrrolidinyl)-8-chloro-6-fluoro-1-methyl-4-oxo-1H,4H-[1,3]thiazeto[3,2-a]quinoline-3-carboxylate To a solution of 1.70 g of ethyl 7-((R)-3-amino-1-pyrrodinyl)-6-fluoro-1-methyl-4-oxo-1H,4H-[1,3]thiazeto[3,2-a]quinoline-3-carboxylate in 5 ml of chlorosulfonic acid, a trace of iodine was added, and the mixture was bubbled with chlorine gas for 2 hours at from 0° C. to 5° C. with stirring. The reaction mixture was poured into ice-water, neutralized to pH 8 with 10% aqueous sodium hydroxide and extracted with chloroform. The extract was dried and evaporated. Ethanol was added to the residue and then filtered. The filtrate was evaporated. Chloroform was added to the residue and then filtered. The filtrate was evaporated to give 0.88 g of pale yellow crystals.

The obtained compound was consistent with that of Example 26.

In the same manner as described in Example 43, the compound of Example 44 was prepared.

EXAMPLE 44

Ethyl 7-((S)-3-amino-1-pyrrolidinyl)-8-chloro-6-fluoro-1-methyl-4-oxo-1H,4H-[1,3]thiazeto[3,2-a]quinoline-3-carboxylate The obtained compound was consistent with that of Example 25.

EXAMPLE 45

Tablet Formulation

| Compound of Example 27 | 100 mg |
|---|---|
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |
| | 210 mg |

EXAMPLE 46

Capsule Formulation

| Compound of Example 27 | 100 mg |
|---|---|
| Lactose | q.s. |
| Carboxymethylcellulose | 15 mg |
| Hydroxypropylcelluose | 2 mg |
| Magnesium stearate | 2 mg |
| | 160 mg |

EXAMPLE 47

Powder Formulation

| Compound of Example 27 | 100 mg |
|---|---|
| Lactose | q.s. |
| D-Mannitol | 500 mg |
| Hydroxypropylcellulose | 5 mg |
| Talc | 2 mg |
| | 1000 mg |

EXAMPLE 48

Injection Formulation

| Compound of Example 27 | 50 mg |
|---|---|
| Glucose | 1000 mg |
| Hydrochloric acid | q.s. |
| Distilled water for injection | q.s. |
| | 20 ml |

EXAMPLE 49

Suppository Formulation

| Compound of Example 27 | 100 mg |
|---|---|
| Hard fat | 1300 mg |

| -continued | |
|---|---|
| | 1400 mg |

What is claimed is:

1. A thiazetoquinoline-3-carboxylic acid compound represented by the formula (I)

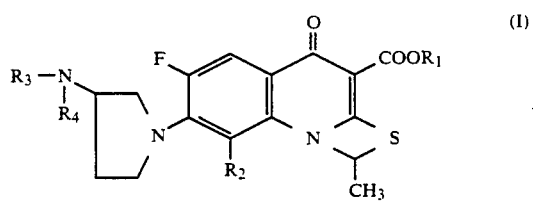

wherein $R_1$ is a hydrogen atom or a lower alkyl group; $R_2$ is a fluorine atom or a chlorine atom; $R_3$ is a hydrogen atom, a lower alkyl group, a lower alkanoyl group, a halogenated lower alkanoyl, or alkoxycarbonyl group; and $R_4$ is a hydrogen atom or a lower alkyl group, or a pharmacologically acceptable salt thereof.

2. 7-((S)-3-amino-1-pyrrolidinyl)-6,8-difluoro-1-methyl-4-oxo-1H,4H-[1,3]thiazeto[3,2-a]quinoline-3-carboxylic acid.

3. 7-((S)-3-amino-1-pyrrolidinyl)-8-chloro-6-fluoro-1-methyl-4-oxo-1H,4H-[1,3]thiazeto[3,2-a]quinoline-3-carboxylic acid.

4. 7-(3-amino-1-pyrrolidinyl)-6,8-difluoro-1-methyl-4-oxo-1H,4H-[1,3]thiazeto[3,2-a]quinoline-3-carboxylic acid.

5. 7-(3-amino-1-pyrrolidinyl)-8-chloro-6-fluoro-1-methyl-4-oxo-1H,4H-[1,3]thiazeto[3,2-a]quinoline-3-carboxylic acid.

6. An antibacterial agent useful for the treatment of bacterial infectious diseases, comprising an effective amount of one or more thiazetoquinoline-3-carboxylic acid compound represented by the formula (I)

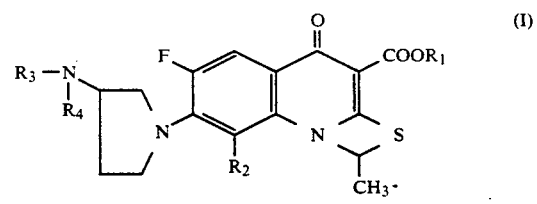

wherein $R_1$ is a hydrogen atom or a lower alkyl group; $R_2$ is a fluorine atom or a chlorine atom; $R_3$ is a hydrogen atom, a lower alkyl group, a lower alkanoyl group, a halogenated lower alkanoyl, or alkoxycarbonyl group; and $R_4$ is a hydrogen atom or a lower alkyl group, or a pharmacologically acceptable salt thereof together with a pharmaceutically acceptable carrier or coating.

7. A pharmaceutical composition useful for the treatment of bacterial infectious disease, comprising an effective amount of one or more thiazetoquinoline-3-carboxylic acid compound represented by the formula (I)

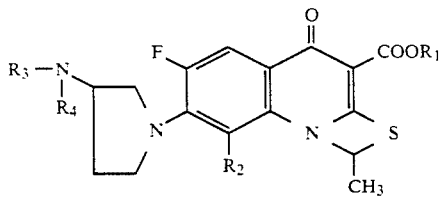

(I)

wherein $R_1$ is a hydrogen atom or a lower alkyl group; $R_2$ is a fluorine atom or a chlorine atom; $R_3$ is a hydrogen atom, a lower alkyl group, a lower alkanoyl group, a halogenated lower alkanoyl, or alkoxycarbonyl group; and $R_4$ is a hydrogen atom or a lower alkyl group, or a pharmaceutically acceptable salt thereof together with a pharmaceutically acceptable carrier or coating.

8. A method for the treatment of bacterial infectious diseases comprising the step of administering to an animal an effective amount of a thiazetoquinoline-3-carboxylic acid compound represented by the formula (I)

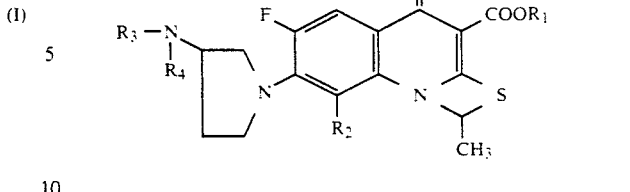

(I)

wherein $R_1$ is a hydrogen atom or a lower alkyl group; $R_2$ is a fluorine atom or a chlorine atom; $R_3$ is a hydrogen atom, a lower alkyl group, a lower alkanoyl group, a halogenated lower alkanoyl, or alkoxycarbonyl group; and $R_4$ is a hydrogen atom or a lower alkyl group; a pharmacologically acceptable salt thereof; an antibacterial agent comprising the same; or a pharmaceutical composition comprising the same.

9. A thiazetoquinoline-3-carboxylic acid compound according to claim 1, wherein $R_1$ is a hydrogen atom; $R_2$ is a fluorine atom or a chlorine atom; $R_3$ is a hydrogen atom; and $R_4$ is a hydrogen atom.

10. A thiazetoquinoline-3-carboxylic acid compound according to claim 1, wherein $R_1$ is a lower alkyl group; $R_2$ is a fluorine atom or a chlorine atom; $R_3$ is a hydrogen atom, a halogenated lower alkanoyl group, or an alkoxycarbonyl group; and $R_4$ is a hydrogen atom.

11. A thiazetoquinoline-3-carboxylic acid compound according to claim 10, wherein $R_1$ is ethyl; and $R_3$ is a hydrogen atom, tert-butoxycarbonyl, or trifluoroacetyl.

* * * * *